United States Patent
Gatto

Patent Number: 5,292,956
Date of Patent: Mar. 8, 1994

[54] HYDROXYPHENYL-SUBSTITUTED AMINE ANTIOXIDANTS

[75] Inventor: Vincent J. Gatto, Baton Rouge, La.

[73] Assignee: Ethyl Corporation, Richmond, Va.

[21] Appl. No.: 937,784

[22] Filed: Sep. 1, 1992

[51] Int. Cl.$^5$ .......... C07C 211/27; C07C 211/29; C10M 133/08

[52] U.S. Cl. .......... 564/374; 564/381; 564/382; 524/81; 524/248; 252/9; 252/401

[58] Field of Search .......... 564/374, 381, 382, 355, 564/219; 524/81, 248, 222; 252/9, 401

[56] References Cited

U.S. PATENT DOCUMENTS

| | | | |
|---|---|---|---|
| 3,043,774 | 7/1962 | Coffield | 524/248 |
| 3,115,466 | 12/1963 | Orloff et al. | 524/248 |
| 3,219,700 | 11/1965 | O'Shea et al. | 260/569 |
| 4,098,760 | 7/1978 | Cornell | 564/211 |

*Primary Examiner*—Richard L. Raymond
*Assistant Examiner*—B. Bembenick
*Attorney, Agent, or Firm*—Patricia J. Hogan

[57] ABSTRACT

Tertiary amines corresponding to the formula $Z_2Z'N$ in which Z is a 3,5-dihydrocarbyl-4-hydroxyphenalkyl group having the structure:

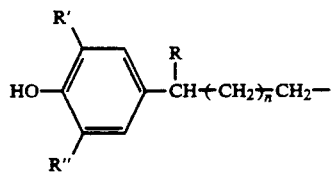

wherein R is hydrogen or an alkyl group of 1-3 carbons; R' and R" are hydrocarbyl groups independently selected from alkyls and cycloalkyls of up to six carbons; n represents zero or one; and Z' is Z or an alkyl, alkenyl, or aralkyl group of up to 18 carbons are novel compounds having antioxidant activity in organic materials which are normally susceptible to oxidative deterioration. They are especially valuable as antioxidants for lubricants.

20 Claims, No Drawings

HYDROXYPHENYL-SUBSTITUTED AMINE ANTIOXIDANTS

FIELD OF INVENTION

This invention relates to novel 3,5-dihydrocarbyl-4-hydroxyphenalkylamines which are suitable for use as antioxidants.

BACKGROUND

Various phenolic compounds have been found to have utility as antioxidants in organic materials which are normally susceptible to oxidative deterioration. Many of these antioxidants—including the secondary and tertiary 3,5-dialkyl-4-hydroxybenzylamines of U.S. Pat. Nos. 3,043,774 (Coffield) and 3,115,466 (Orloff et al.) and the N,N-bis(3,5-dialkyl-4-hydroxyphenalkyl)amides of U.S. Pat. 5,120,792 (Gatto)—can be used to stabilize a variety of materials against oxidative degradation but have limited use in lubricants and other oils because of being solids with low solubility in oils. It would be desirable to find antioxidants which would have sufficient solubility in such materials, as well as in other normally oxidizable organic materials, and have melting points and degrees of volatility and thermal stability such as to make them more useful in stabilizing the materials against oxidative degradation.

SUMMARY OF INVENTION

The invention resides in (1) novel 3,5-dihydrocarbyl-4-hydroxyphenalkylamines corresponding to the formula $Z_2Z'N$ in which Z is a 3,5-dihydrocarbyl-4-hydroxyphenalkyl group having the structure:

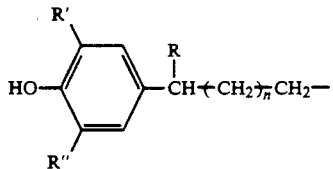

wherein R is hydrogen or an alkyl group of 1–3 carbons; R' and R" are hydrocarbyl groups independently selected from alkyls and cycloalkyls of up to six carbons; n represents zero or one; and Z' is Z or an alkyl, alkenyl, or aralkyl group of up to 18 carbons and (2) their use as antioxidants for normally oxidizable materials, especially polymers and lubricating oils.

DETAILED DESCRIPTION

The compounds of the invention are tertiary amines in which at least two of the N-substitutents are 3,5-dihydrocarbyl-4-hydroxyphenalkyl groups and any remaining N-substituent is an alkyl, alkenyl, or aralkyl group of up to 18 carbons. Like the tertiary amines of Coffield and Orloff et al., they show antioxidant activity in organic materials which are normally susceptible to oxidative deterioration.

The present amines differ from those of Coffield and Orloff et al. in having a longer carbon chain separating the 3,5-dihydrocarbyl-4-hydroxyphenyl groups from the amino nitrogen and in having lower volatility, better thermal stability, and higher solubility in natural and synthetic oils. These properties give them a considerable advantage over the known antioxidants in that (1) their lower volatility and better thermal stability permit them to be used in higher temperature applications and (2) their higher solubility makes them considerably easier to formulate into fuels and oils and even permits the preparation of concentrates, which are the preferred vehicle for introducing antioxidants into such materials.

Another advantage of the novel amines is their being oils or low-melting solids which—unlike the higher melting N,N-bis(3,5-dialkyl-4-hydroxyphenalkyl)amides of Gatto —can be introduced into normally oxidizable materials under moderate conditions, e.g., the relatively low temperatures used for processing polyethylene and some polypropylenes.

Among the amines of the invention, those which are preferred are apt to vary with the application in which they are to be used. For example, as in known antioxidants, the compounds having greater steric hindrance of the phenolic hydroxy group are generally more effective antioxidants; but it may sometimes be desirable to reduce this steric hindrance, as by using a compound having methyl and t-butyl o-substituents instead of two t-butyl substituents, to improve solubility. Moreover, although the compounds in which —CH(R)—(CH$_2$-)$_n$—CH$_2$— is —CH$_2$—CH$_2$— are frequently preferred, those in which R is alkyl and/or n is 1 may be preferred for use in organic materials, such as polymers, in which it can be important to avoid discoloration by the antioxidant.

Exemplary of the compounds of the invention are N,N,N-tris[β-(3,5-di-t-butyl-4hydroxyphenyl)ethyl]amine; N,N,N-tris[β-(3,5-di-t-butyl-4-hydroxyphenyl)-β-(methyl)ethyl]-amine;N,N,N-tris[β-(3,5N,N,N-tris[β-(3,5-di-t-butyl-4-hydroxyphenyl)-β-(isopropyl)ethyl]amine; N,N,N-tris[γ-(3,5-di-t-butyl-4-hydroxyphenyl)propyl]amine; N,N,N-tris[γ-(3,5-di-t-butyl-4-hydroxyphenyl)-γ-(ethyl)propyl]amine; the corresponding N,N,N-tris(3,5-dihydrocarbyl-4-hydroxyphenalkyl)amines in which at least one of the t-butyl groups is replaced with methyl, ethyl, propyl, isopropyl, butyl, isobutyl, cyclopentyl, or cyclohexyl; and the corresponding N,N-bis(3,5-dihydrocarbyl-4-hydroxyphenalkyl)amines in which one of the 3,5-dihydrocarbyl-4-hydroxyphenalkyl groups of the tris compounds is replaced with methyl, ethyl, propyl, butyl, hexyl, octyl, decyl, dodecyl, hexadecyl, octadecyl, allyl, methallyl, benzyl, 3,5-di-t-butyl-4-hydroxybenzyl, or phenethyl; and mixtures thereof.

The manner in which the $Z_2Z'N$ tertiary amines of the invention are prepared is not critical. They may be synthesized by any of the techniques conventionally employed for the preparation of tertiary amines. For example:

(A) The N,N,N-tris[3,5-dihydrocarbyl-4-hydroxyphenalkyl]amines ($Z_3N$) may be prepared by a process in which (1) a 4-cyanoalkyl-2,6-dihydrocarbylphenol is prepared by (a) reacting the sodium salt of the corresponding 2,6-dihydrocarbylphenol with acrylonitrile as in U.S. Pat. No. 2,903,487 (Coffield) or (b) reacting the 2,6-dihydrocarbylphenol with an aldehyde and hydrochloric acid followed by treatment with sodium cyanide as in Netherlands Patent Application 7905000 (Cincinnati Milacron Chemicals), (2) the 4-cyanoalkyl-2,6-dihydrocarbylphenol is coupled in the presence of hydrogen, a hydrogenation catalyst, and a suitable solvent to produce a mixture of primary ($ZNH_2$), secondary ($Z_2NH$), and tertiary ($Z_3N$) amines and (3) either (a) the $Z_3N$ is recovered from the mixture or (b) the $ZNH_2/Z_2NH/Z_3N$ mixture is further alkylated to form a mixture of $ZZ'_2N$, $Z_2Z'N$, and $Z_3N$.

(B) The N,N-bis[3,5-dihydrocarbyl-4-hydroxyphenalkyl]alkylamines ($Z_2Z'N$) may be prepared by (1) alkylation of the secondary amine $Z_2NH$ with the appropriate alkyl chloride, bromide, or iodide in the presence of a base and a suitable solvent or (2) reductive alkylation of the secondary amine $Z_2NH$ with the appropriate aldehyde in the presence of a hydrogenation catalyst and a suitable solvent.

When the synthesis is conducted so as to prepare an amine mixture—either a mixture composed primarily of one or more tertiary amines of the invention or a mixture also containing a substantial amount of the corresponding primary and/or secondary amines, the mixture is apt to be useful per se because of the antioxidant activity of all of the amine components. However, the amine mixtures may be resolved whenever a pure or substantially pure tertiary amine is desired or when it is important to remove excessive amounts of ingredients other than the amines of the invention. For example, when the amine product is to be employed in an application wherein the greater volatility or poorer thermal stability of the primary and/or secondary amines would make the product less effective, it is desirable to resolve the mixtures containing such amines so as to provide amine products in which the primary and/or secondary amine content is not more than minimal, e.g., 0–10% by weight of the product.

Whether the starting material is a 2,6-dihydrocarbylphenol or an intermediate obtained therefrom, the source of the 3,5-dihydrocarbyl-4-hydroxyphenyl portion of the novel amines should be one in which the hydrocarbyl substituents are alkyl and/or cycloalkyl groups of up to six carbons, e.g., methyl, ethyl, propyl, isopropyl, butyl, isobutyl, t-butyl, cyclopentyl, or cyclohexyl. These o-hydrocarbyl substituents may be the same (as when the starting material is 2,6-dimethylphenol, 2,6-diisopropylphenol, 2,6-di-t-butylphenol, or 2,6-dicyclohexylphenol), or they may be different (as when the starting material is 2-methyl-6-t-butylphenol, 2-ethyl-6-cyclohexylphenol, or 2-isopropyl-6-t-butylphenol).

The source of the $-CH(R)-(CH_2)_n-CH_2-$ portion of the novel amines, as indicated above, may be a secondary amine which already contains such a group or a reactant or combination of reactants which provide such a group. The reactants capable of providing this substituent will be apparent to those skilled in the art and include, in addition to the compounds specifically taught above, aldehydes such as methanal, ethanal, propanal, isopropanal, and the butanals. A preferred source is the N,N-bis[$\beta$-(3,5-di-t-butyl-4-hydroxyphenyl)ethyl]amine of U.S. Pat. No. 4,098,760 (Cornell).

As already mentioned, the Z' of the tertiary amine may be provided by a primary amine, chloride, bromide, or iodide containing the Z' group or by an aldehyde which, together with hydrogen, generates that Z' group. Exemplary of the compounds that may be used as sources of Z' are the methyl, ethyl, propyl, butyl, hexyl, octyl, decyl, dodecyl, hexadecyl, octadecyl, allyl, methallyl, benzyl, 3,5-di-t-butyl-4-hydroxybenzyl, phenethyl, 3,5-diisopropyl-4-hydroxyphenethyl, and 3-methyl-5-t-butyl-4-hydroxyphenethyl amines, chlorides, bromides, and iodides, as well as aldehydes such as formaldehyde, acetaldehyde, propionaldehyde, butyraldehyde, hexaldehyde, octyl aldehyde, decyl aldehyde, dodecyl aldehyde, hexadecyl aldehyde, octadecyl aldehyde, and benzaldehyde.

The tertiary amines of the invention may be incorporated into a variety of organic materials as antioxidants, the organic materials being those which are normally susceptible to oxidative deterioration, e.g.:

(1) natural oils (including animal oils, vegetable oils, oils derived from coal and shale, and solvent-refined or acid-refined mineral oils) and synthetic oils (including poly-$\alpha$-olefins, esters of dicarboxylic acids, and silicon-based oils), such as those used as lubricating oils, turbine oils, transformer oils, transmission fluids, glass annealing oils, gear and machine lubricants, hydraulic lubricants, and crankcase oils, (2) fuels, such as gasolines, diesel fuels, domestic heating oils, and bunker and residual fuel oils, (3) natural polymers, such as cellulose, rubber, proteins, and their derivatives, (4) synthetic resins, such as epoxy resins, polycarbonates, polyurethanes, polyureas, polyamides, polyesters, polyethers, phenol-formaldehyde resins, urea-formaldehyde resins, and melamine-formaldehyde resins, (5) polymers and interpolymers of ethylenically-unsaturated hydrocarbons, such as ethylene, propylene, butylene, isobutylene, styrene, butadiene, and piperylene, including the homopolymers, copolymers, and other interpolymers thereof with one another, and copolymers and interpolymers of at least one of them with one or more copolymerizable nonhydrocarbons, such as vinyl acetate, acrylonitrile, methacrylonitrile, methyl acrylate, and methyl methacrylate, (6) halogen-containing polymers, such as polyvinyl chloride and fluoride, polyvinylidene chloride, vinyl chloride-vinylidene chloride copolymers, polychloroprene, and chlorinated rubbers, (7) other vinyl and allyl polymers, such as polyvinyl alcohol, acetate, stearate, benzoate, maleate, and butyral, polyallylmelamine, and polyallyl phthalate, and (8) acrylic polymers, such as polyacrylates, polymethacrylates, polyacrylamides, polyacrylonitrile, and polymethacrylonitrile.

In particularly preferred embodiments of the invention, the organic materials stabilized with the tertiary amines are lubricating oils or polymers of ethylenically-unsaturated monomers, especially polyolefins such as polyethylenes and polypropylenes.

The organic materials which are stabilized in accordance with the present invention may contain additives of the types conventionally employed in such materials, including synergists, such as the dialkyl phosphonates of Orloff et al., the teachings of which are incorporated herein by reference. The amount of the tertiary amine incorporated into the organic material is an antioxidant amount, generally at least 0.003%, based on the weight of the organic material. When the tertiary amine is incorporated into the total amount of organic material to be stabilized, its concentration is usually about 0.005–5%, preferably about 0.01–2%, based on the weight of the organic material. However, much higher amounts of the antioxidant, e.g., up to 25% by weight or more, may be incorporated into the organic material if desired—as when it is most convenient to mix the antioxidant with the majority of a fuel or lubricant composition in the form of a concentrate.

The following examples are given to illustrate the invention and are not intended as a limitation thereof.

EXAMPLE 1

Preparation of N,N-Bis[β-(3,5-di-t-butyl-4-hydroxyphenyl)ethyl]octylamine

Stir a solution of 4.5 g (9.3 mmols) of N,N-bis[β-(3,5-di-t-butyl-4-hydroxyphenyl)ethyl]amine, 1.8 g (9.3 mmols) of 1-bromooctane, and 2.0 g (18.7 mmols) of sodium carbonate in 50 mL of acetonitrile for 17 hours at reflux temperature. Add another 0.3 g (1.6 mmols) of 1-bromooctane and stir at reflux for an additional 18 hours. After cooling, concentrate the reaction mixture, in vacuo, dissolve the resulting oil in 50 mL of toluene, and wash with water (2×50 mL). Dry the organic phase over magnesium sulfate and concentrate in vacuo. Flash column chromatography (120 g silica gel 60, 230–400 mesh, EM), using heptane followed by 1.5% isopropyl alcohol/heptane as the eluting solvents, gives 3.3 g (60.0%) of N,N-bis[β-(3,5-di-t-butyl-4-hydroxyphenyl)ethyl]octylamine as a slightly colored oil which GC area % analysis shows to be 99.0% pure.

H-NMR (in CDCl$_3$): δ0.88 (t, 3H), 1.25–1.34 (m, 10H), 1.44–1.57 (s and m, 38H), 2.56–2.61 (m, 2H), 2.67–2.81 (m, 8H), 5.05 (s, 2H), 7.01 (s, 4H).

IR (in C$_6$D$_6$): 3630, 2960, 2920, 2880, 2860, 1435, 1330, 1230 cm$^{-1}$.

GC-MS: m/e 592.5 (M+), 494.4, 374.3, 233.2, 57.1.

EXAMPLE 2

Preparation of N,N-Bis[β-(3,5-di-t-butyl-4-hydroxyphenyl)ethyl]stearylamine

Repeat Example 1 except for replacing the 9.3+1.6 mmols of 1-bromooctane with 9.3 mmols of 1-bromooctadecane (all of which is present in the initial reaction mixture) and refluxing for 23 hours. The process gives 2.3 g (33.3%) of N,N-bis[β-(3,5-di-t-butyl-4-hydroxyphenyl)ethyl]stearylamine as a slightly colored oil.

H-NMR (in CDCl$_3$): δ0.88 (t, 3H), 1.23–1.34 (m, 30H), 1.43–1.56 (s and m, 38H), 2.56–2.61 (m, 2H), 2.67–2.81 (m, 8H), 5.05 (s, 2H), 7.02 (s, 4H).

IR (in C$_6$D$_6$): 3635, 2960, 2920, 2870, 2850, 1430, 1325, 1230 810, 805 cm$^{-1}$.

MW by HRMS: Exact Mass Calcd for C$_{50}$H$_{86}$NO$_2$ 732.666, Obsd 732.667.

EXAMPLE 3

Preparation of N,N-Bis[β-(3,5-di-t-butyl-4-hydroxyphenyl)ethyl]methylamine

Charge a suitable reaction vessel with 3.0 g (6.2 mmols) of N,N-bis[β-(3,5-di-t-butyl-4-hydroxyphenyl)ethyl]amine, 2.2 g of 37% formaldehyde (27.1 mmols), 0.6 g of 10% Pd/C, and 15 mL of n-butanol. Purge with hydrogen and shake the vessel on a Parr Series 3900 Hydrogenation Apparatus at 60 psi (0.4 MPa) hydrogen pressure and room temperature for 5 hours. Dilute the resulting slurry with 30 mL of methylene chloride, filter, and concentrate the filtrate in vacuo to give 3.1 g of N,N-bis[β-(3,5-di-t-butyl-4-hydroxyphenyl)ethyl]methylamine as a yellow oil which slowly crystallizes on standing. GC area % analysis shows the product to be 98.8% pure.

H-NMR (in CDCl$_3$): δ1.43 (s, 36H), 2.42 (s, 3H), 2.65–2.71 (m, 4H), 2.72–2.78 (m, 4H), 5.07 (s, 2H), 7.01 (s, 4H).

IR (in C$_6$D$_6$): 3620, 2940, 2900, 2860, 1430, 1230, 1150 cm$^{-1}$.

GC-MS: 276.2 (M+ −219), 233.2, 57.1.

EXAMPLE 4

Preparation of N,N,N-Tris[β-(3,5-di-t-butyl-4-hydroxyphenyl)ethyl]amine

Part A

Charge a suitable reaction vessel with 50.0 g (0.20 mol) of α-(3,5-di-t-butyl-4-hydroxyphenyl)acetonitrile, 10.0 g of 10% Pd/C, and 200 mL of anhydrous ethanol. Purge with hydrogen and shake the vessel on a Parr Series 3900 Hydrogenation Apparatus at 60 psi (0.4 MPa) hydrogen pressure and room temperature for 22 hours. Dilute the resulting slurry with 200 mL of methylene chloride, filter, and concentrate the filtrate in vacuo to give 50.5 g of a thick oil which GC area % analysis and H-NMR analysis (normalized to 100%) show to consist mainly of 77.6% N,N-bis[β-(3,5-di-t-butyl-4-hydroxyphenyl)ethyl]amine, 19.8% N,N,N-tris[β-(3,5-di-t-butyl-4-hydroxyphenyl)ethyl]amine, and 2.6% N-β-(3,5-di-t-butyl-4-hydroxyphenyl)ethylamine.

Part B

Subject 5.3 g of the product of Part A to flash column chromatography as in Example 1. Combine all fractions containing the desired N,N,N-tris[β-(3,5-di-t-butyl-4-hydroxyphenyl)ethyl]amine, concentrate in vacuo, and further purify the resulting oil by preparative thin layer chromatography (Analtech silica gel GF, 2000 micron plates) using 3% isopropyl alcohol/hexanes as the developing solvent system. The product is 0.70 g of N,N,N-tris[β-(3,5-di-t-butyl-4-hydroxyphenyl)ethyl]amine which GC area % analysis shows to be 96.6% pure.

H-NMR (in CDCl$_3$): δ1.44 (s, 54H), 2.75–2.81 (m, 6H), 2.85–2.91 (m, 6H), 5.07 (s, 3H), 7.04 (s, 6H).

IR (in C$_6$D$_6$): 3630, 2960, 2920, 1435, 1330, 1230, 815, 810 cm$^{-1}$.

MW by HRMS: Exact Mass Calcd for C$_{48}$H$_{74}$NO$_3$ 712.567, Obsd 712.567.

EXAMPLE 5

Mixture of N,N-Bis[β-(3,5-di-t-butyl-4-hydroxyphenyl)ethyl]hexylamine and N,N,N-Tris[β-(3,5-di-t-butyl-4-hydroxyphenyl)ethyl]amine Stir a solution of 5.7 g of the product of Example 4, Part A, 3.6 g (21.6 mmols) of 1-bromohexane, 2.3 g (21.6 mmols) of sodium carbonate, and 50 mg (0.333 mmol) of sodium iodide in 20 mL of acetonitrile for five hours at reflux temperature and then concentrate the reaction mixture in vacuo. Add the residue to a mixture of 50 mL of heptane, 50 mL of toluene, and 50 mL of water to dissolve all solids and residue oil. Separate the phases, sequentially wash the organic portion with water (2×50 mL) and 50 mL of saturated NaCl, dry over magnesium sulfate, and concentrate in vacuo. Dissolve the resulting oil in 50 mL of toluene, heat at 50° C. for ten minutes in the presence of 1.0 g of activated carbon, cool, filter through a pad of silica gel 60 (4.0 g, 230–400 mesh, EM), and wash the pad with 50 mL of toluene. Then concentrate the combined filtrate and wash in vacuo to give 4.4 g of an orange viscous oil containing 78.9% N,N-bis[β-(3,5-di-t-butyl-4-hydroxyphenyl)ethyl]hexylamine and 17.0% N,N,N-tris[β-(3,5-di-t- butyl-4-hydroxyphenyl)ethyl]amine by GC area % analysis.

EXAMPLE 6

Mixture of N,N-Bis[β-(3,5-di-t-butyl-4-hydroxyphenyl)ethyl]octylamine and N,N,N-Tris[β-(3,5-di-t-butyl-4-hydroxyphenyl)ethyl]amine Stir a solution of 21.2 g of the product of Example 4, Part A, 10.2 g (42.6 mmols) of 1-iodooctane, and 4.5 g (42.6 mmols) of sodium carbonate in 80 mL of acetonitrile for four hours at reflux temperature and cool overnight. Then reflux the reaction mixture for an additional 1.5 hours, add 1.0 g (4.2 mmols) of 1-iodooctane, reflux for another 0.5 hour, add 1.0 g (4.2 mmols) of 1-iodooctane, reflux for 0.5 hour, add 2.0 g (8.4 mmols) of 1-iodooctane, reflux for another 0.5 hour, add a final charge of 2.0 g (8.4 mmols) of 1-iodooctane, continue heating for 1.5 hours, and then cool and concentrate the reaction mixture in vacuo. Dissolve the residue and salts in 100 mL of toluene and 50 mL of water, separate the phases, sequentially wash the organic portion with water (2×50 mL) and 50 mL of saturated NaCl, and dry over magnesium sulfate. Heat the toluene solution to 50° C., treat it with 1.0 g of activated carbon for 10 minutes, cool, filter, and concentrate in vacuo. Strip the resulting oil of excess 1-iodooctane, dissolve the product in 150 mL of refluxing hexanes, separate the soluble and insoluble materials by decantation, concentrate the hexane solution to 50 mL, and pass the concentrate through a flash column (75 g silica gel 60, 230–400 mesh, EM) using 2% isopropyl alcohol/hexanes as the eluting solvent. Then combine all fractions containing the product and concentrate in vacuo to give 11.6 g of a red oil containing 79.2% N,N-bis[β-(3,5-di-t-butyl-4-hydroxyphenyl)ethyl]octylamine and 14.0% N,N,N-tris[β-(3,5-di-t-butyl-4-hydroxyphenyl)ethyl]amine by GC area % analysis.

EXAMPLE 7

Property Evaluations

Compare properties of (A) the products of Examples 1–6, (B) certain tertiary amines of Coffield, and (C) two antioxidants commonly used in polymers and/or oils by calculating their molecular weights and determining their melting points, volatility, and solubility in Petro-Canada hydro treated [70% 80N, 30% 160N] base oil with low sulfur. The results of these evaluations are shown in Tables I and II.

| Codes for Antioxidants Used in This and Subsequent Examples | |
|---|---|
| Code | Name of Compound |
| AN-1 | N,N-bis[β-(3,5-di-t-butyl-4-hydroxyphenyl)ethyl]octylamine |
| AN-2 | N,N-bis[β-(3,5-di-t-butyl-4-hydroxyphenyl)ethyl]stearylamine |
| AN-3 | N,N-bis[β-(3,5-di-t-butyl-4-hydroxyphenyl)ethyl]methylamine |
| AN-4 | N,N,N-tris[β-(3,5-di-t-butyl-4-hydroxyphenyl)ethyl]amine |
| AN-5 | 4.6/1 mixture of N,N-bis[β-(3,5-di-t-butyl-4-hydroxyphenyl)ethyl]hexylamine and N,N,N-tris[β-(3,5-di-t-butyl-4-hydroxyphenyl)ethyl]amine (~96% pure) |
| AN-6 | 5.7/1 mixture of N,N-bis[β-(3,5-di-t-butyl-4-hydroxyphenyl)ethyl]octylamine and N,N,N-tris[β-(3,5-di-t-butyl-4-hydroxyphenyl)ethyl]amine (~93% pure) |
| C-3 | N,N-bis(3,5-di-t-butyl-4-hydroxybenzyl)methylamine |
| C-4 | N,N-tris(3,5-di-t-butyl-4-hydroxybenzyl)amine |
| E-330 | 1,3,5-trimethyl-2,4,6-tris(3,5-di-t-butyl-4-hydroxybenzyl)benzene |
| E-702 | bis(3,5-di-t-butyl-4-hydroxyphenyl)methane |

TABLE I

Melting Points and Volatility

| Compound | MW | Melting Point (°C.) Onset by DSC | Temperature (°C.) at 50% Weight Loss in $N_2$ | Temperature (°C.) at 50% Weight Loss in Air |
|---|---|---|---|---|
| E-702 | 424.7 | 155.8 | 253.1 | 259.5 |
| C-3 | 467.7 | 181.4 | 231.7 | 231.9 |
| AN-3 | 495.8 | 78.1 | 294.7 | 287.7 |
| AN-5 | | oil | 318.7 | 308.0 |
| AN-1 | 594.1 | oil | 324.4 | 308.4 |
| AN-6 | | oil | 322.1 | 306.9 |
| C-4 | 672.1 | 260.3 | 297.6 | 268.1 |
| AN-4 | 714.1 | glass | 343.0 | 324.1 |
| AN-2 | 734.3 | oil | 356.4 | 337.9 |
| E-330 | 775.2 | 167.5; 246.0 | 382.2 | 368.7 |

TABLE II

Solubility in a Base Oil at 25° C.

| Antioxidant | Concentration of Antioxidant in Oil | | |
|---|---|---|---|
| | 1 Wt. % | 10 Wt. % | 25 Wt. % |
| E-702 | Soluble | Insoluble | — |
| C-3 | Insoluble | — | — |
| AN-3 | Soluble | Hazy | Insoluble |
| AN-1 | Soluble | Soluble | Soluble |
| C-4 | Insoluble | — | — |
| AN-4 | Soluble | Soluble | Soluble |
| AN-2 | Soluble | Soluble | Soluble |
| E-330 | Insoluble | — | — |

As demonstrated above, particularly with regard to C-3 vs. AN-3 and C-4 vs AN-4, which differ from one another only in the length of the chain separating the 3,5-dihydrocarbyl-4-hydroxyphenyl groups from the amino nitrogen, the compounds of the invention have much greater solubility in the oil than the comparable compounds of Coffield. The Coffield amines are insoluble at a concentration as low as 1%, while the present amines are still soluble at a concentration of 25%. The present amines are also much less volatile than the amines of Coffield.

EXAMPLE 8

Test of Antioxidants in Petroleum Oil

Prepare a series of samples by dissolving 0.5% by weight of an antioxidant in (A) Petro-Canada hydro treated [70% 80N, 30% 160N] base oil with low sulfur, or (B) a Petro-Canada base oil partially formulated with the components that make up a typical crankcase oil. Determine the oxidation induction times for the oils in accordance with the method reported in Walker et al., "Characterization of Lubricating Oils by Differential Scanning Calorimetry," SAE Technical Paper Series No. 801383, National Bureau of Standards, Chemical Kinetics Div., Baltimore, Md., 1980, using an oxygen gas purge at a pressure of 500 psi (3.4 MPa), a flow of 120 cc/minute (NTP), and a temperature of 185° The results of the test are shown in Table III.

TABLE III

| | Oxidation Induction Times in Oil | |
|---|---|---|
| | Induction Time (minutes) | |
| Antioxidant | In Unformulated Oil | In Formulated Oil |
| None | 4.2 | 11.7 |
| E-702 | 15.7 | — |
| AN-1 | 14.8 | 27.7 |
| AN-2 | 15.1 | — |
| AN-3 | — | 30.2 |
| AN-4 | 14.2 | — |

EXAMPLE 9

Test of Antioxidants in Poly-α-olefin Oil

Dissolve 1.0% by weight of AN-6 in one aliquot of Ethylflo®164 poly-α-olefin containing 3% by weight of tricresyl phosphate. Subject it and an unstabilized aliquot of the tricresyl phosphate-containing poly-α-olefin to an oxidation corrosion test by heating 25 mL of oil at 175° C. in the presence of copper and steel coupons and bubbling air through the oil at a rate of 5 liters/hour for 18 hours. The results of the test are shown in Table IV.

TABLE IV

| | Stabilization of Poly-α-olefin | | |
|---|---|---|---|
| Antioxidant | % Viscosity Increase | Cu Weight Loss (mg) | Fe Weight Loss (mg) |
| none | 36.8 | 1.38 | 0.07 |
| AN-6 | 0.60, 0.60* | 0.41, 0.49* | 0.11, 0.16* |

*Duplicate run

EXAMPLE 10

Test of Antioxidants in Polypropylene

Part A

Prepare three blends of polypropylene powder, 0.05% by weight of calcium stearate as an acid neutralizer and lubricating agent, and 0.1% by weight of AN-1, AN-2, and E-330, respectively.

Part B

Extrude the compositions of Part A in a Brabender twin screw extruder at 150°-245°-245° C. and 30 rpm under nitrogen, quench and pelletize the extended compositions, retain a portion of the pellets of each of the compositions for testing, and extrude the remaining pellets through a Brabender single screw extruder at 260° C. and 30 rpm with ambient air, making five passes and retaining samples after the first, third, and fifth passes for testing. Then test the extruded samples for melt flow index and yellowness index. The results of the test are shown in Table V.

TABLE V

| | MFI @ 230° C./2160 g Extrusion Passes | | | Yellowness Index Extrusion Passes | | |
|---|---|---|---|---|---|---|
| Stabilizer | ss1 | ss3 | ss5 | ss1 | ss3 | ss5 |
| AN-1 | 4.9 | 5.7 | 7.2 | 6.8 | 10.2 | 14.0 |
| AN-2 | 5.8 | 6.1 | 8.0 | 5.9 | 10.2 | 11.1 |
| E-330 | 7.5 | 11.5 | 16.5 | 4.9 | 5.3 | 7.3 |

What is claimed is:

1. A 3,5-dihydrocarbyl-4-hydroxyphenalkylamine corresponding to the formula $Z_2Z'N$ in which Z is a 3,5-dihydrocarbyl-4-hydroxyphenalkyl group having the structure:

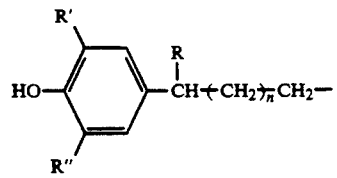

wherein R is hydrogen or an alkyl group of 1-3 carbons; R' and R" are hydrocarbyl groups independently selected from alkyls and cycloalkyls of up to six carbons; n represents zero or one; and Z' is Z or an alkyl, alkenyl, or aralkyl group of up to 18 carbons.

2. The 3,5-dihydrocarbyl-4-hydroxyphenalkylamine of claim 1 wherein n is zero, R is hydrogen, and Z' is Z.

3. The 3,5-dihydrocarbyl-4-hydroxyphenalkylamine of claim 2 which is N,N,N-tris[β-(3,5-di-t-butyl-4-hydroxyphenyl)ethyl]amine.

4. The 3,5-dihydrocarbyl-4-hydroxyphenalkylamine of claim 1 wherein n is zero, R is hydrogen, and Z' is an alkyl, alkenyl, or aralkyl group of up to 18 carbons.

5. The 3,5-dihydrocarbyl-4-hydroxyphenalkylamine of claim 4 wherein Z' is alkyl.

6. The 3,5-dihydrocarbyl-4-hydroxyphenalkylamine of claim 5 which is N,N-bis[β-(3,5-di-t-butyl-4-hydroxyphenyl)ethyl]methylamine, N,N-bis[β-(3,5-di-t-butyl-4-hydroxyphenyl)ethyl]hexylamine, N,N-bis[β-(3,5-di-t-butyl-4-hydroxyphenyl)ethyl]octylamine, or N,N,bis[β-(3,5-di-t-butyl-4-hydroxyphenyl)ethyl]-stearylamine.

7. The 3,5-dihydrocarbyl-4-hydroxyphenalkylamine of claim 1 wherein n is zero, R is alkyl, and Z' is Z.

8. The 3,5-dihydrocarbyl-4-hydroxyphenalkylamine of claim 1 wherein n is zero, R is alkyl, and Z' is an alkyl, alkenyl, or aralkyl group of up to 18 carbons.

9. The 3,5-dihydrocarbyl-4-hydroxyphenalkylamine of claim 1 wherein n is one, R is hydrogen, and Z' is Z.

10. The 3,5-dihydrocarbyl-4-hydroxyphenalkylamine of claim 1 wherein n is one, R is hydrogen, and Z' is an alkyl, alkenyl, or aralkyl group of up to 18 carbons.

11. The 3,5-dihydrocarbyl-4-hydroxyphenalkylamine of claim 1 wherein n is one, R is alkyl, and Z' is Z.

12. The 3,5-dihydrocarbyl-4-hydroxyphenalkylamine of claim 1 wherein n is one, R is alkyl, and Z' is an alkyl, alkenyl, or aralkyl group of up to 18 carbons.

13. The 3,5-dihydrocarbyl-4-hydroxyphenalkylamine of claim 1 wherein the 3,5-dihydrocarbyl-4-hydroxyphenyl group is 3,5-diisopropyl-4-hydroxyphenyl, 3,5-di-t-butyl-4-hydroxyphenyl, 3,5-dicyclohexyl-4-hydroxyphenyl, or 3-methyl-5-t-butyl-4-hydroxyphenyl.

14. A composition which comprises an organic material that is normally susceptible to oxidative deterioration and an antioxidant amount of a 3,5-dihydrocarbyl-4-hydroxyphenalkylamine of claim 1.

15. The composition of claim 14 wherein the organic material is a hydrocarbon lubricating oil.

16. The composition of claim 15 wherein the lubricating oil is a mineral oil.

17. The composition of claim 15 wherein the lubricating oil is a poly-α-olefin.

18. The composition of claim 14 wherein the organic material is a polymer of an ethylenically-unsaturated monomer.

19. The composition of claim 18 wherein the polymer is a polyolefin.

20. The composition of claim 19 wherein the polyolefin is polypropylene.

* * * * *